United States Patent

Frese

Patent Number: 5,851,820
Date of Patent: Dec. 22, 1998

[54] UNIT FOR THE PREPARATION OF FERMENTING GAS

[76] Inventor: Christoph Frese, Twangweg 13, 59964, Medebach, Germany

[21] Appl. No.: 801,474

[22] Filed: Feb. 18, 1997

[51] Int. Cl.$^6$ ................................................ C17M 3/00
[52] U.S. Cl. ............................ 435/289.1; 435/286.7; 435/291.7; 435/295.1; 435/813; 422/225; 366/147; 366/241; 366/271
[58] Field of Search ..................... 435/289.1, 286.7, 435/291.7, 295.1, 813, 818; 422/129, 135, 198, 225; 366/147, 241, 271

[56] References Cited

FOREIGN PATENT DOCUMENTS 41 13 000 A1  10/1992  Germany ................. C02F 11/04

*Primary Examiner*—David A. Redding
*Attorney, Agent, or Firm*—J.M. Mark Gilbreth; Robert W. Strozier; Gilbreth & Strozier, P.C.

[57] ABSTRACT

A unit for the preparation of fermenting gas by fermenting viscous media with mixing paddles that can be moved continuously back and forth and in the same direction in the tank to mix the medium to be fermented. Alternately, the mixing paddles hang from a rotating roller in the tank and the roller is driven such that the mixing paddles are moved up and down. The unit may be fitted with several mixing paddles arranged in series and in the direction of the mixing effect, i.e., the suspended mixing paddles are arranged above each other in the event of a vertical tank, in which case a joint drive unit is provided for each mixing paddle group, thus moving the mixing paddles simultaneously in such a manner that each individual mixing paddle executes only a limited stroke, but the mixing paddles as a whole achieve a complete mixing of the medium to be fermented in the chamber, in which are installed the mixing paddles. The heat exchange is improved, when a heat exchange wall is installed between the two chambers.

9 Claims, 3 Drawing Sheets

UNIT FOR THE PREPARATION OF FERMENTING GAS

BACKGROUND OF THE INVENTION

1. Field of the Invention

The presented invention concerns a unit for the preparation of fermenting gas by fermenting viscous media with the help of mixing paddles that continuously move back and forth in one direction in the tank to mix the medium to be fermented.

2. Brief Description of the Related Art

A unit of this type used to prepare fermenting gas is known from the document DE 41 13 000 (A1). In this known unit, the mixing of the medium to be fermented in the fermenting chambers is achieved with mixing paddles that move up and down in the tank. Furthermore, there is another chamber that is initially reached by the supplied medium to be fermented and that will be called heating chamber in the following; the unit also exhibits a fourth chamber that is reached by the medium to be fermented after leaving the fermenting chambers, i.e., a so-called discharge chamber. The heating as well as discharge chambers are fitted with mixing paddles that hang from a rotating roller in the tank and are moved up and down with a rotating of the roller, thus mixing the medium to be fermented in the heating and discharge chamber. Because a heat exchange wall is installed between these two chambers, the mixing must be particularly thorough to utilize the very different temperatures between the entering medium to be fermented that is relatively cold and the discharging medium to be fermented that is relatively warm, i.e., to recover heat. The disadvantage of this known unit for the preparation of fermenting gas consists in the fact that the mixing paddles installed in the heating and discharge chambers as well as the two mixing paddles for the larger fermenting chamber must cover the whole stroke through the tank prior to reversing their direction. Accordingly, an individual mixing paddle must mix the whole medium to be fermented over the filling height in the tank. It is quite clear that it takes a relatively long time for the mixing paddle to travel from its highest point (point of reversal) just below the level of the medium to be fermented in the tank to its lowest point, in which case this time period has been doubled, when the mixing paddle again reaches the highest point.

SUMMARY OF THE INVENTION

Accordingly, the task of the presented invention consists in the making available of a unit for the preparation of fermenting gas by fermenting viscous media of the above-mentioned type, with which it is possible to achieve a more effective mixing of the medium to be fermented. In a unit designed in accordance with a preferred variant of the invention, in which a heat exchanger wall is fitted between the heating and discharge chambers, the more effective mixing process is also accompanied by an improved heat exchange effect.

The solution for the above-mentioned task yields a unit of the type described earlier with the characteristic feature indicated in the main claim. In accordance with the invention, several mixing paddles are arranged in series and in the direction of the mixing process and are moved with a joint drive unit providing a simultaneous moving of the mixing paddles, thus ensuring that individual mixing paddles move only with a limited stroke; the mixing paddles as a whole, however, affect a complete mixnng of the medium to be fermented in the chamber, in which the mixing paddles move back and forth in one direction.

In a preferred manner, the tank that is used for this unit and contains the medium to be fermented is a vertical tank and the mixing direction, in which the medium to be fermented is to be mixed, is vertical; the mixing is achieved with approximately horizontal mixing paddles that can be moved up and down in the tank. In such a preferred arrangement, the mixing paddles can hang from a suspension arrangement designed such that its operation achieves a moving up and down of the mixing paddles.

The invention provides two groups of mixing paddles that can be suspended side-by-side from a suspension arrangement in the tank, in which case the individual mixing paddles of a group will be arranged above each other. In a preferred manner, the medium to be fermented will be mixed by the suspension arrangement in such a manner that one group of mixing paddles located above each other moves up, while the other group of mixing paddles arranged laterally moves down simultaneously, or vice versa. The suspension arrangement can be designed such that the two mixing paddle groups are in an equilibrium.

In accordance with a preferred further development of the solution to the invention's task, the two mixing paddle groups hang from a roller. This roller rotates about its shaft and is fitted with an eccentric cam that produces an upward movement for one mixing paddle group and, simultaneously, a downward movement for the other mixing paddle group, and vice versa. With this arrangement, it is also possible to advantageously use the fact that the larger mixing paddles provided for the mixing of the medium to be fermented in the two main fermenting chambers can also be suspended in this manner, thus requiring one roller and one single drive unit for the mixing with all mixing paddles in the different chambers, i.e., also for those installed in the heating and discharge chamber.

In a preferred manner, the suspension arrangement is also fitted with two pressure arms and the lower end of the eccentric cam is fitted with a pressure roller that pushes one of the pressure arms down, in which case the other pressure arm is free and moves up, thus producing some type of a pendulum movement for the two mixing paddle groups. Since several mixing paddles are arranged above each other and since they provide a simultaneous mixing effect at different heights of the medium to be fermented, each mixing paddle must cover a shorter stroke distance than a single mixing paddle used for the whole tank height. Accordingly, this arrangement yields a more frequent and thus a more effective mixing of the medium to be fermented.

In accordance with a preferred design of the invention, the suspension arrangement may exhibit a first arm, to which is fitted the first mixing paddle groups, and a second arm, to which is fitted the second group of mixing paddles, in which case the two arms can be arranged in a rotating manner around a central shaft in the connection area, i.e., in the form of a pendulum. Each of the above-mentioned pressure arms is in a preferred manner rigidly connected with one arm each by way of a strut to stiffen this arrangement. Again in a preferred manner, one mixing paddle group is in a rotating manner and by way of a roller suspended at the end of the arm, for example, and in such a manner that the mixing paddles hang approximately in a horizontal position during the pendulum-like movement of the arms.

In a preferred manner and as indicated earlier, this tank type is fitted with a heating and discharge chamber. For that reason, and in a preferred manner, a first group of mixing paddles is suspended in the heating chamber and a second mixing paddle group in the discharge chamber, in which case a heat exchange wall is arranged between the heating and discharge chamber. However and in accordance with the invention, the mixing effect is not limited to such a tank type and to the above-mentioned heating or discharge chambers, but can generally be applied to the mixing of media to be fermented in fermenting gas units of this type.

When a heat exchanger wall is fitted between the two chambers, it is preferred to provide several parallel cross-stabilizers to stabilize the heat exchange wall particularly in large tanks of this type. The sub-claims describe preferred further developments to solve the task in accordance with the invention. The following detailed description lists further advantages of the invention.

DETAILED DESCRIPTION OF THE INVENTION

In the following, presented invention shall be described in more detail with the help of the enclosed drawings.

Figure 1:
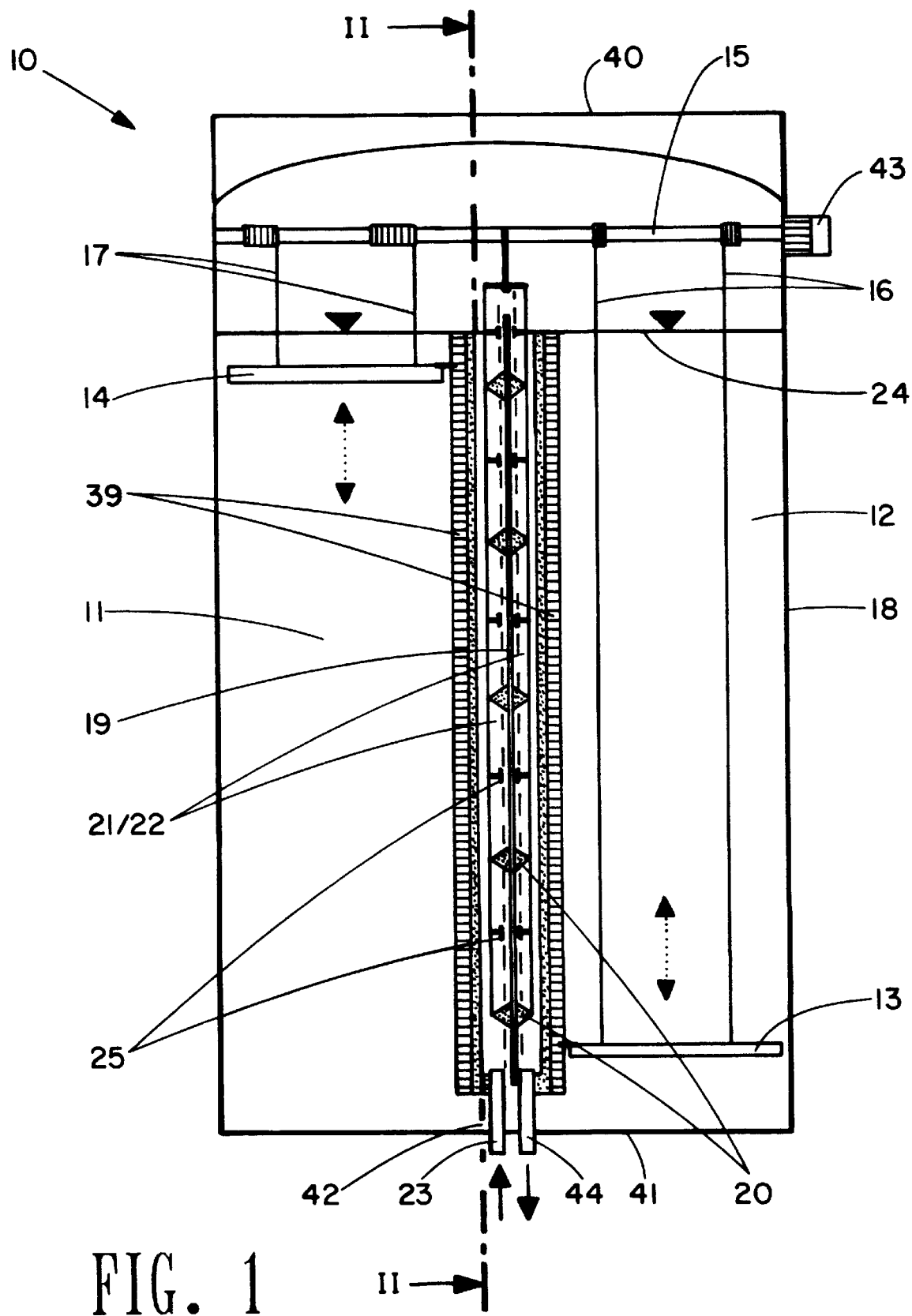
FIG. 1 shows a longitudinal section through a tank in accordance with the invention that is used for the fermenting of viscous media.

Reference is made first to FIG. 1. The unit in accordance with the invention and used to prepare fermenting gas exhibits a possibly cylindrical or rectangular tank 10 that is covered at the top with cover 40 or similar and contains the medium to be fermented 24 consisting of a viscous organic medium that can be fermented such as liquid manure or similar. By way of supply opening 23 arranged at tank floor 41, the fresh medium to be fermented first reaches the possibly rectangular heating chamber 21 and subsequently rises in this heating chamber 21. A pump can be used to pump the fresh medium to be fermented to this heating chamber 21. When the medium that is to be fermented and is pumped into heating chamber 21 has reached the top of the heating chamber, it flows across a separating wall into a first fermenting chamber 11.

This first fermenting chamber 11 is by way of opening 42 at the floor connected to a second fermenting chamber 12. These two fermenting chambers 11, 12 are fitted with mixing paddles 14, 13 respectively that are plate-like and suspended in the tank from a rotating roller 15, i.e., with the help of ropes 16 or 17 that serve as the suspension arrangement. Roller 15 can be rotated by way of drive 43 to move mixing paddles 14, 13 up or down in tank 10, i.e., by coiling or uncoiling ropes 16 or 17. Heating areas 39 are provided in the region of the inside wall in the two fermenting chambers 11, 12.

As indicated in FIG. 1, the fermented medium leaves the second and right fermenting chamber 12 and enters discharge chamber 22, which it leaves by way of drain 44 arranged in the floor of tank 10. Separating wall 19 between heating chamber 21 and discharge chamber 22 is formed by heat exchanger 19. Thus a heat exchange acheived between the fresh medium that is to be fermented is relatively cold particularly during the winter. It reaches heating chamber 21 by way of supply opening 23 and the fermented discharging medium to be fermented that exhibits a relatively high temperature and is discharged by way of discharge chamber 22.

Figure 2:
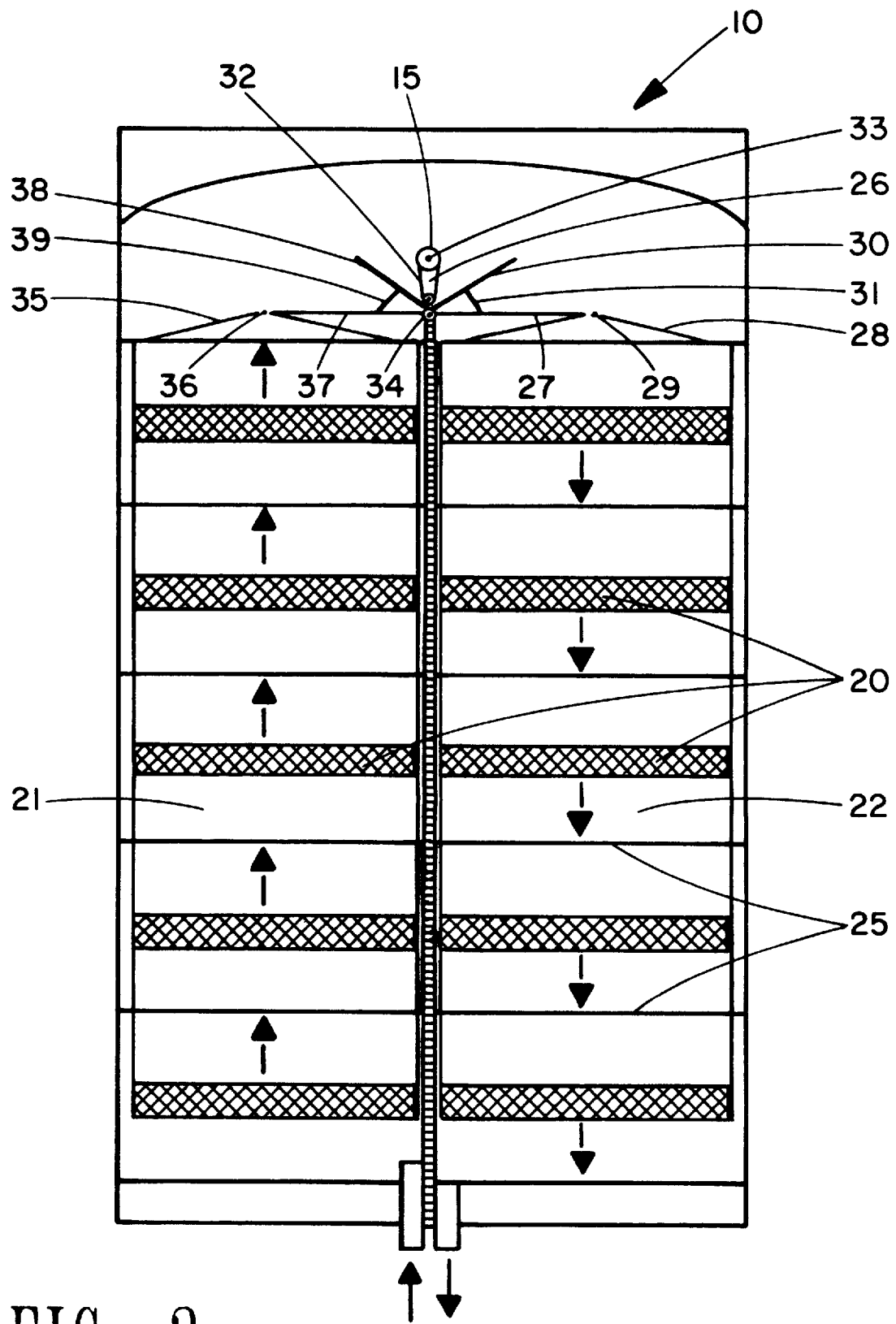
FIG. 2 shows a section through the tank as indicated by line II in FIG. 1.
Figure 3:
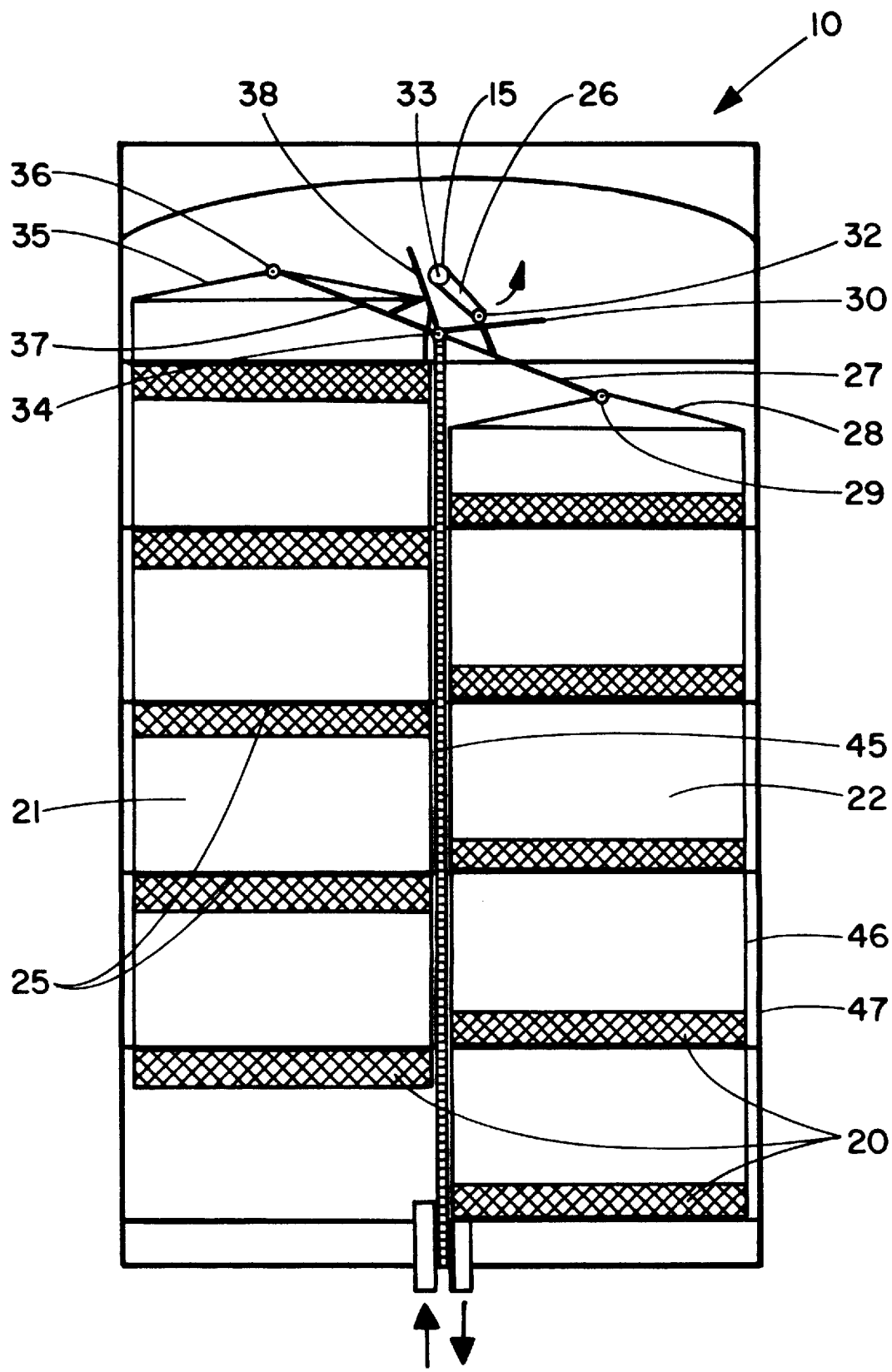
FIG. 3 shows a corresponding section through the tank and similar to FIG. 2; however, the mixing paddles are in a different position.

Heating chamber 21 and discharge chamber 22 are fitted with the respective mixing paddles 20 to achieve a continuous, uniform and careful mixing of the medium to be fermented in this chamber. These mixing paddles 20 can also move up and down in heating chamber 21 and discharge chamber 22. The same drive is used to move the mixing paddles up or down, i.e., roller 15 that can be rotated with drive 43 about shaft 33 as indicated in FIG. 2. In accordance with the invention, several of these mixing paddles 20 are arranged at a spacing above each other in heating chamber 21 as well as in discharge chamber 22, in which case one group of such mixing paddles 20 moves up with a rotating of roller 15 and the other group of mixing paddles 20 in the other chamber moves down simultaneously, and vice versa. Said mixing principle and the device used to obtain this effect, i.e., the special suspension arrangement used for mixing paddles 20, shall be explained in the following in more detail with the help of FIGS. 2 and 3.

It can be seen that eccentric cam 26 is attached to the rotating roller 15 arranged in the central area of tank 10. Each group of mixing paddles 20 used in each of the two chambers 21, 22 is served by a suspension arrangement consisting of suspension unit 28 with a central roller 29 that can rotate about its shaft and is arranged at the end of beam-like arm 27 that at its other end is arranged to rotate about horizontal shaft 34. In a corresponding manner, arm 37 is arranged in the other chamber 21 to rotate about shaft 34, to which is attached by way of roller 36 suspension unit 35, from which are suspended mixing paddles 20 for heating chamber 21. Since one of suspension units 28 or 35 always supports a group of mixing paddles 20, two ropes 45, 46 lead down vertically and hold the lower mixing paddles 20.

As indicated in FIG. 2, arm 27 as well as arm 37 is aligned horizontally in the initial position of eccentric cam 26, i.e., when it is aligned vertically and downward. Laterally of this horizontally aligned arm 27, to which is fastened suspension unit 28 for mixing paddles 20, is provided pressure arm 30 that can rotate about shaft 34 arranged at the center of tank 10. In a similar manmer, the other group of mixing paddles 20 is served by pressure arm 38 that is arranged on the other side and rotates about the same shaft 34. Pressure arm 30 is by way of connection strut 31 that runs perpendicular to it connected to arm 27 and pressure arm 38 is in a similar manner and by way of strut 39 connected to the other arm 37. In the horizontal initial position of the two arms 27, 37 as shown in FIG. 2, the two pressure arms 30, 38 are aligned at an acute angle and in an inclined manner toward the top. When eccentric cam 26 moves by rotating roller 15 about its shaft 33, pressure roller 32 pushes on pressure arm 30 at the lower end of the eccentric cam when it is moved counter-clockwise and thus pushes it down. The movement of eccentric cam 26 is indicated with an arrow in FIG. 3. In that manner, arm 27 moves with pressure arm 30 down in a rotating motion about shaft 34; suspension unit 28 and with it mixing paddles 20 move down to reach the position indicated in FIG. 3. In that manner, the medium to be fermented is mixed in discharge chamber 22. Arm 37 that is rigidly connected to arm 27 also moves simultaneously and clockwise about shaft 34 and reaches its upper position, thus causing suspension unit 35 and mixing paddles 20 to move up from the position indicated in FIG. 2 to reach the position indicated in FIG. 3, thus achieving a mixing of the medium to be fermented in heating chamber 21. Eccentric cam 26 with its arm subsequently moves in the opposite direction of rotation, i.e., it rotates clockwise, and the mixing paddles in discharge chamber 22 move up, eccentric cam 26 pushes on the left pressure arm 38 and the mixing paddles in heating chamber 21 move beyond the initial position indicated in FIG. 2. In other words, there is a constantly changing up and down movement as indicated by the arrows in FIG. 2, thus achieving a continuous mixing effect. In that regard, the stroke of mixing paddles 20 executed in both chambers 21, 22 amounts to only a fraction of the height of tank 20 /sic/ as a function of the mixing paddle distance, i.e., the use of five mixing paddles reduces the stroke to only approximately one fifth of the whole fluid level height of the medium to be fermented in the tank. Since one uses several mixing paddles 20 arranged above each other and since all mixing paddles move up and down, each moving up or down of mixing paddles 20 always ensures that the whole medium to be fermented will be mixed in the two chambers 21, 22. Thus is achieved a more intensive mixing and also a more effective heat recovery by means of heat exchanger wall 19 arranged at the center between chambers 21, 22. The stabilization of this vertical heat exchanger wall 19 is achieved with transverse stabilizers 25 that are shown in FIG. 1 and also in FIG. 3 and in both chambers 21, 22 extend from the tank's center outward to the outside tank wall 47. In FIG. 1, the tank wall running perpendicular to this tank wall is indicated with number 18.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

All patent, patent applications and articles cited herein, are hereby incorporated by reference for all that they disclose and suggest.

What is claimed is:

1. A unit for the preparation of fermenting gas by fermenting viscous media comprisng:
   a) a tank comprising a chamber for mixing the medium to be fermented;
   b) several mixing paddles in the tank continuously movable in a vertical direction of mixing;
   c) a joint drive unit connected to and for simultaneously moving the mixing paddles where the joint drive operates such that each individual mixing paddle moves only a limited stroke distance in the direction of mixing;
   d) a suspension unit connected to and dividing the several paddles into a first group of linearly aligned mixing paddles and a second group of linearly aligned mixing paddles, with the first and second groups arranged side-by-side in the tank, and wherein the suspension unit operates to move the first group of mixing paddles up then down while simultaneously moving the second group of mixing paddles down then up; and wherein the suspension unit further comprises two pressure arms connected to an eccentric cam having a lower end, wherein the lower end of the eccentric cam is fitted with a pressure roller that pushes one of the pressure arms down, with the other pressure arm free to reach an upper position, producing a pendulum type movement.

2. The unit of claim 1 wherein a support strut is rigidly connected to each of the two pressure arms.

3. The unit of claim 2 wherein one of the group of mixing paddles is suspended by way of a suspension unit and a roller installed at the end of one of the arms.

4. The unit of claim 3 wherein the chamber comprises a heat exchanger wall forming a heating chamber and a discharge chamber, and wherein said first group of mixing paddles is suspended in a heating chamber and said second group of mixing paddles is suspended in a discharge chamber.

5. The unit of claim 4 wherein the heat exchanger wall is fitted with several parallel transverse stabilizers.

6. The unit of claim 1 wherein the suspension arrangement comprises a first arm supporting the first group of mixing paddles, and a second arm supporting the second group of mixing paddles, wherein the two arms are rotatable in a pendulum fashion about a central shaft arranged at a center between the two arms.

7. The unit of claim 6 wherein one of the group of mixing paddles is suspended by way of a suspension unit and a roller installed at the end of one of the arms.

8. The unit of claim 1 wherein the chamber comprises a heat exchanger wall forming a heating chamber and a discharge chamber, and wherein a first group of mixing paddles is suspended in a heating chamber and a second group of mixing paddles is suspended in a discharge chamber.

9. The unit of claim 8 wherein the heat exchanger wall is fitted with several parallel transverse stabilizers.

* * * * *